(12) United States Patent
Vellaisamy et al.

(10) Patent No.: US 10,634,654 B2
(45) Date of Patent: Apr. 28, 2020

(54) ELECTROCHEMICAL DETECTOR

(71) Applicant: City University of Hong Kong, Kowloon (HK)

(72) Inventors: A. L. Roy Vellaisamy, Kowloon (HK); Shishir Venkatesh, Shatin (HK); Chi-Chung Yeung, Sheung Shui (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 15/393,336

(22) Filed: Dec. 29, 2016

(65) Prior Publication Data
US 2018/0188222 A1 Jul. 5, 2018

(51) Int. Cl.
*G01N 33/02* (2006.01)
*G01N 27/22* (2006.01)
*G01N 27/414* (2006.01)

(52) U.S. Cl.
CPC ........... *G01N 33/02* (2013.01); *G01N 27/221* (2013.01); *G01N 27/4145* (2013.01)

(58) Field of Classification Search
CPC .............................. G01N 33/02; G01N 27/221
See application file for complete search history.

(56) References Cited

U.S. PATENT DOCUMENTS

| | | | |
|---|---|---|---|
| 4,921,591 A * | 5/1990 | Mochizuki ......... | G01N 27/3335 204/412 |
| 6,974,716 B2 | 12/2005 | Hsiung et al. | |
| 7,164,162 B2 | 1/2007 | Hsiung et al. | |
| 7,598,546 B1 | 10/2009 | Chou et al. | |
| 8,384,409 B2 | 2/2013 | Kummel et al. | |
| 2006/0046375 A1 | 3/2006 | Chou et al. | |
| 2006/0148118 A1 | 7/2006 | Hsiung et al. | |
| 2006/0197118 A1* | 9/2006 | Migliorato ....... | G01N 33/54373 257/253 |
| 2009/0278175 A1 | 11/2009 | Chou et al. | |
| 2013/0210641 A1 | 8/2013 | Rothberg et al. | |
| 2014/0348707 A1* | 11/2014 | King Smith ....... | G01N 27/4148 422/82.03 |
| 2014/0370636 A1 | 12/2014 | Dalton et al. | |

OTHER PUBLICATIONS

Haupt, Karsten, and Klaus Mosbach. "Molecularly imprinted polymers and their use in biomimetic sensors." Chemical Reviews 100.7 (2000): 2495-2504.*

Al-Hardan, Naif H., et al. "High sensitivity pH sensor based on porous silicon (PSi) extended gate field-effect transistor." Sensors 16.6 (2016): 839.*

Estrela, Pedro, and Piero Migliorato. "Chemical and biological sensors using polycrystalline silicon TFTs." Journal of Materials Chemistry 17.3 (2007): 219-224.*

(Continued)

*Primary Examiner* — Robert J Eom
(74) *Attorney, Agent, or Firm* — Renner Kenner Greive Bobak Taylor & Weber (57) ABSTRACT

An electrochemical detector including at least one substance selection structure disposed adjacent or proximate to an electronic device structure, wherein the substance selection structure is arranged to interact with a target substance having a molecular structure so as to alter an electrical characteristic of the electronic device structure.

18 Claims, 7 Drawing Sheets

(56) References Cited

OTHER PUBLICATIONS

Guzinski, M. et al., "Lead(II)-selective ionophores for ion-selective electrodes: A review", Analytica Chimica Acta, vol. 791, pp. 1-12, 2013.
Bobacka, J., "Conducting Polymer-Based Solid-State Ion-Selective Electrodes", Electroanalysis, vol. 18, pp. 7-18, 2006.
Zia, A. I., et al., "Rapid and molecular selective electrochemical sensing of phthalates in aqueous solution." Biosensors and Bioelectronics, vol. 67, pp. 342-349, 2015.

* cited by examiner

ELECTROCHEMICAL DETECTOR

TECHNICAL FIELD

The present invention relates to an electrochemical detector, although not exclusively, to an electrochemical detector for detecting plasticizer.

BACKGROUND

Food poisoning is one of the most serious public health problems everywhere around the world. Various harmful additives or contaminants in food may affect the health of the general public. Therefore, the quality of food must be regularly examined to ensure that some poisonous or hazardous substances do not exceed safety levels.

The concentration of these harmful substances may be determined by using testing agents. The traditional chemical testing approaches are time consuming and may not respond promptly. Alternatively, material characterization techniques in laboratories may be used to analyse the concentration of a target substance and even the composition of a testing sample. Although the results may be very accurate and sensitive, these techniques used in laboratories may not be suitable for daily applications which require prompt and low-cost testing results.

SUMMARY OF THE INVENTION

In one example embodiment, the present invention is advantageous in that it provides for improvement over conventional devices by providing improved detection limit in the neighbourhood of ppb level, without increase in production complexity.

In accordance with a first aspect of the present invention, there is provided an electrochemical detector comprising a substance selection structure disposed adjacent or proximate to an electronic device structure, wherein the substance selection structure is arranged to interact with a target substance having a molecular structure so as to alter an electrical characteristic of the electronic device structure.

In an embodiment of the first aspect, the substance selection structure arranged to interact with at least one molecule of the target substance.

In an embodiment of the first aspect, the substance selection structure includes a molecule-selective electrode.

In an embodiment of the first aspect, the molecule-selective electrode comprises a polymer layer arranged to accommodate the at least one molecule, and wherein the target substance is in contact with the polymer layer.

In an embodiment of the first aspect, the polymer layer includes a plurality of voids each arranged to accommodate a molecule of the target substance.

In an embodiment of the first aspect, each of the plurality of voids includes a structure matching with a molecular structure of the at least one molecule.

In an embodiment of the first aspect, the plurality of voids are selective to the target substance.

In an embodiment of the first aspect, the polymer layer includes a molecular imprinted polymer.

In an embodiment of the first aspect, the molecular imprinted polymer includes a plurality of polymer particles each having a size of around 50 μm.

In an embodiment of the first aspect, the electrical characteristic of the electronic device structure is altered when the polymer layer accommodates the at least one molecule.

In an embodiment of the first aspect, the electrical characteristic of the electronic device structure is altered by a change in a differential capacitance of the substance selection structure.

In an embodiment of the first aspect, the electrical characteristic of the electronic device structure is altered by a change in a permittivity and/or a dielectric constant of the polymer layer accommodating the at least one molecule.

In an embodiment of the first aspect, the electrochemical detector further comprises an intermediate substrate arranged to connect the substance selection structure and the electronic device structure.

In an embodiment of the first aspect, the intermediate substrate includes a copper substrate.

In an embodiment of the first aspect, the intermediate substrate is further arranged to electrically connect the substance selection structure and the electronic device structure.

In an embodiment of the first aspect, the substance selection structure and the electronic device structure are fabricated on a plurality of separate substrates.

In an embodiment of the first aspect, the plurality of separate substrates includes a plurality of doped silicon substrates.

In an embodiment of the first aspect, the electronic device structure includes a transistor.

In an embodiment of the first aspect, the substance selection structure is arrange to operate as a gate electrode of the transistor.

In an embodiment of the first aspect, the electrical characteristic includes a threshold voltage of the transistor.

In an embodiment of the first aspect, the electrical characteristic includes a saturation drain current across the transistor under a predetermined gate bias and a predetermined source-drain bias.

In an embodiment of the first aspect, the target substance includes plasticizer.

In accordance with a second aspect of the present invention, there is provided a method for fabricating an electrochemical detector in accordance with the first aspect, the method comprises the steps of: fabricating the substance selection structure and the electronic device structure on one or more substrates; and electrically and physically connecting the substance selection structure and the electronic device structure.

In an embodiment of the second aspect, the step of fabricating the substance selection structure comprises the step of: fabricating a combination of a molecular-imprinted polymer and a molecular template of the target substance using a polymerization process; extracting and removing the molecular template from the molecular-imprinted polymer; and depositing the molecular-imprinted polymer on the substrate to form a molecule-selective electrode.

In an embodiment of the second aspect, the step of fabricating the substance selection structure further comprises the step of grounding and sieving the combination of the molecular-imprinted polymer and the molecular template to obtain a plurality of polymer particles each having a size of around 50 μm.

In accordance with a second aspect of the present invention, there is provided a method for detecting a target substance with the electrochemical detector in accordance with the first aspect, the method comprises the steps of: applying an analyte solution containing a predetermined amount of the target substance to the at least one substance selection structure; applying a gate voltage to the thin-film transistor via the analyte solution and the at least one substance selection structure; applying a source-drain bias to the thin-film transistor; and determining a concentration of the target substance in the analyte solution based on a characterization of the electrical characteristic of the transistor.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENT

The inventors have, through their own research, trials and experiments, devised that plasticizers which are commonly found in plastic, especially polyvinyl chloride, may be used for increasing the fluidity of a material. However, being in contact with excess amount of plasticizers will affect our health. There are several ortho-phthalate plasticizers have been classified as potential endocrine disruptors.

Gas chromatography-mass spectrometry (GC-MS) may be applied to detect plasticizers, but the instrument is big in size and expensive, and it requires a trained person to operate. As such this equipment is accessible to the general public. Therefore, inexpensive, quick and user friendly devices as pre-screening tools may be preferable for detecting plasticizers in aqueous solutions.

Preferably, thin film transistor (TFT) based sensors may be used due to their low cost and simple fabrication process. On the other hand, modular design which may enable the combinations to different types of chemical receptors for different applications. In addition, these modular devices may be fabricated by printing in large and flexible substrates.

In one example embodiment of the present invention, electrochemical sensors based on selective bonding of plasticizers in aqueous phase. The sensor may be used to detect extremely low levels (ppb) of plasticizers with appropriate receptors or sensing electrodes, thus providing a cost-effective, accurate and reliable means for plasticizers detection in aqueous media, such as water or other liquids.

Figure 1:
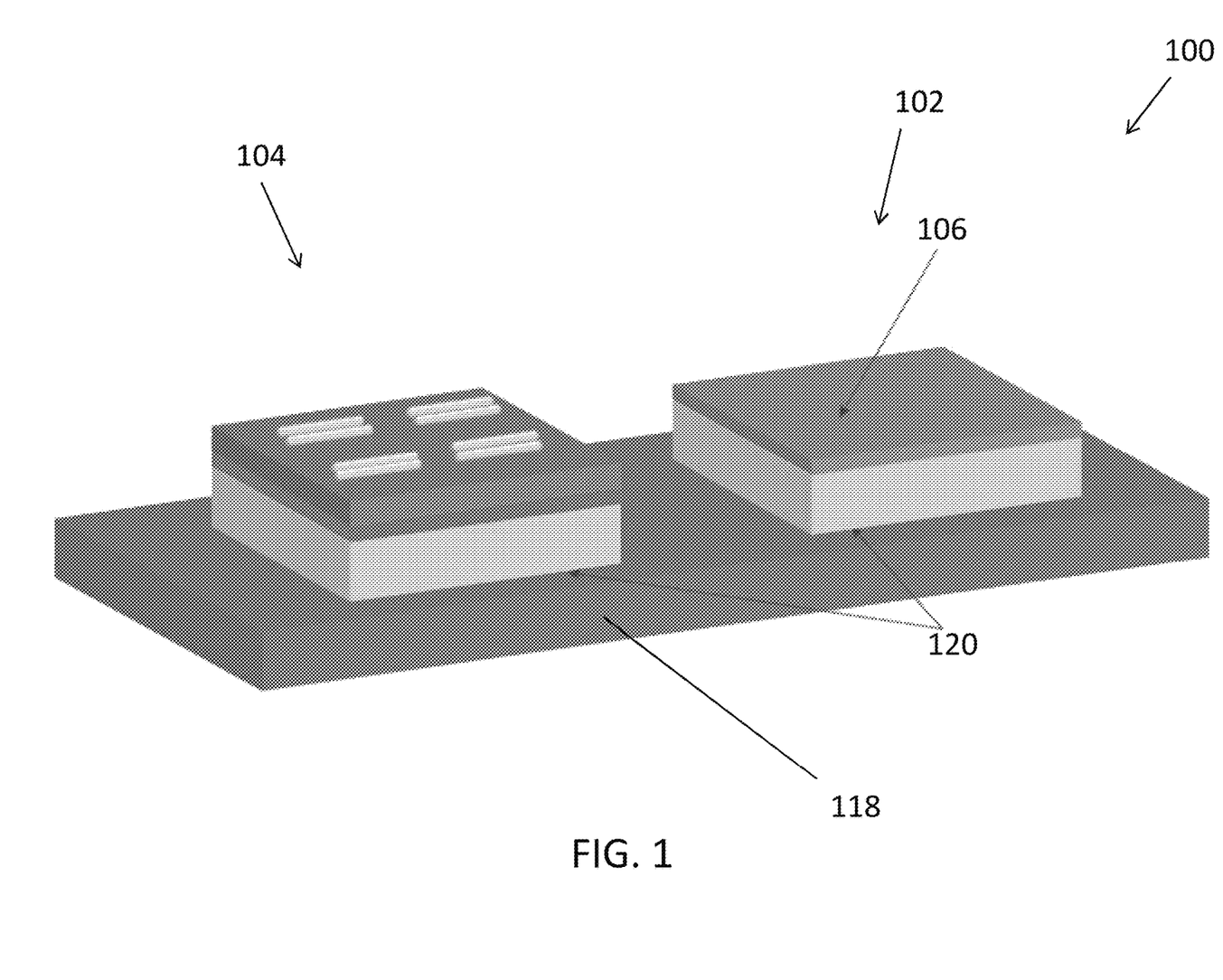
FIG. 1 is a perspective view of an electrochemical detector in accordance with one embodiment of the present invention.

With reference to FIG. 1, there is shown an example embodiment of an electrochemical detector 100 comprising at least one substance selection structure 102 disposed adjacent or proximate to an electronic device structure 104, wherein the substance selection structure 102 is arranged to interact with a target substance having a molecular structure so as to alter an electrical characteristic of the electronic device structure 104.

In this embodiment, the electrochemical detector 100 comprises a substance selection structure 102 which includes chemical receptors arranged to interact with other chemical substance which is in contact with the substance selection structure 102, and the interaction is transformed to an electrical signal which may be further captured or detected by an electronic device structure 104. For example, a drop of analyte solution may be disposed on a surface of the substance selection structure 102, chemical receptors in the substance selection structure 102 may react/interact with the target substance in the analyte solution, and the substance selection structure 102 may produce an electrical signal to be detected by the electronic device structure 104 upon the chemical reaction. Alternatively, the substance selection structure 102 may alter an electrical characteristic, such as a resistance/impedance value of the electronic device structure 104 in response to a change in an electrical/physical characteristic (such as capacitance, permittivity, dielectric constant, etc.) of the substance selection structure 102.

Preferably, the substance selection structure 102 includes a molecule-selective electrode, and the substance selection structure may interact with at least one molecule of the target substance.

The molecule-selective electrode 102 may be specifically designed for facilitating the detection of plasticizer molecules in the target substance.

Alternatively, the molecule-selective electrode 102 may include different structures and/or components for the detection of different/multiple target substances.

Figure 2:
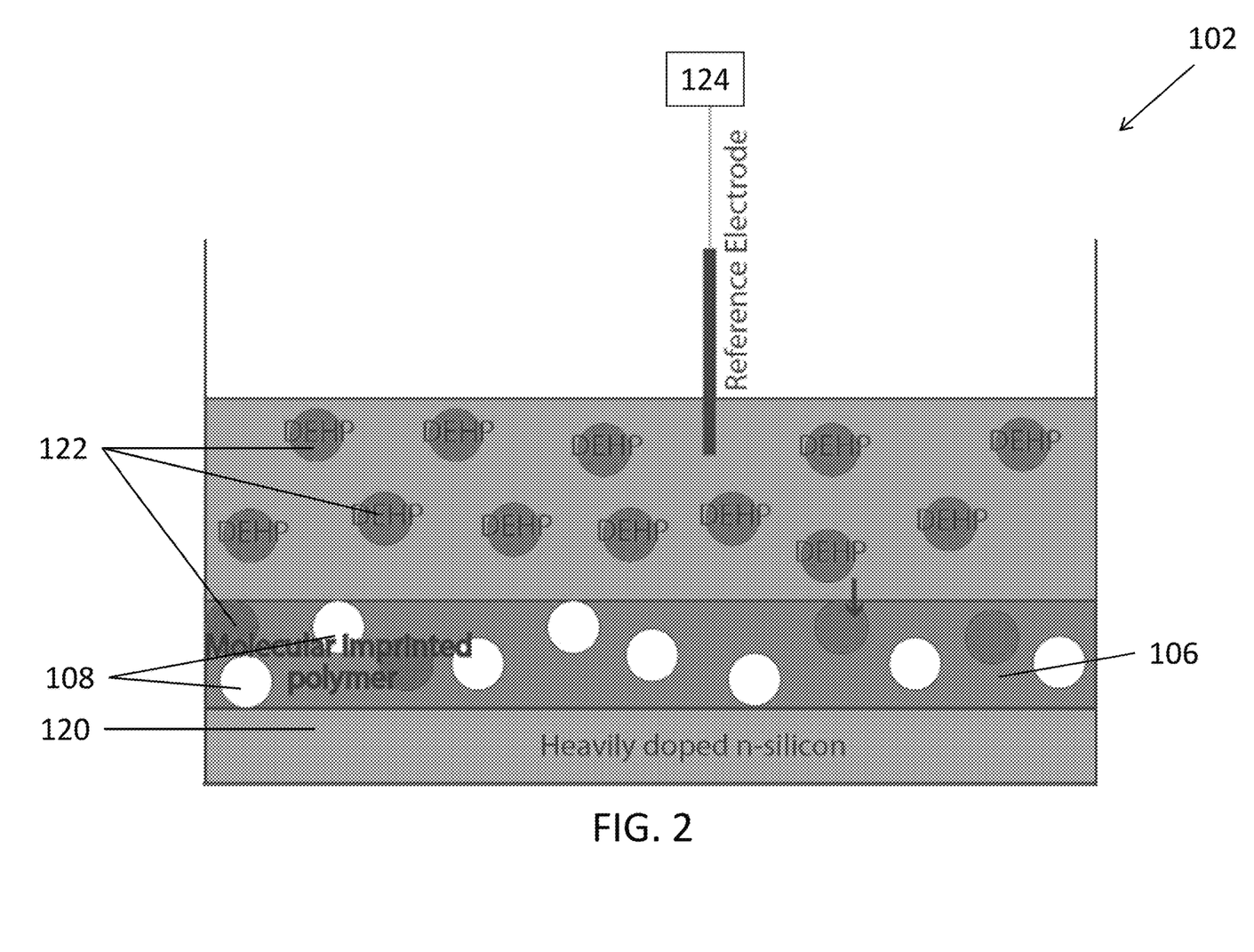
FIG. 2 is an illustration showing a cross-section of the substance selection structure and an interaction of between a molecule of the target substance and the substance selection structure of the electrochemical detector of FIG. 1.

With reference to the example embodiment as shown FIG. 2, the molecule-selective electrode 102 comprises a polymer layer 106. Preferably, the polymer layer may include a molecular imprinted polymer, in which the polymer layer 106 is provided with a plurality of voids each arranged to accommodate a molecule of the target substance, therefore the polymer layer 106 may accommodate the molecules of the target substance when the target substance is in contact with the polymer layer 106.

In this example embodiment, each of the plurality of voids 108 includes a structure (such as a molecular structure) matching with a molecular structure of the molecules of the target substance. Hence, the voids 108 are selective to the target substance and may accommodate only the matching molecules of the target substance. The polymer layer 106 will not interact with substance with any molecular structures which do not match with the molecular imprinted structure.

Referring to FIG. 2, when the target substance is in contact with the target substance 122, the voids 108 accommodate one or more molecules of the target substance 122. Upon the interaction between the target substance and the substance selection structure 102, the permittivity and hence the dielectric constant and the electrical capacitance of the molecular imprinted polymer layer 106 is changed, therefore it may subsequently alter the electrical characteristic of the electronic device structure 104 which is in electrical communication with the substance selection structure 102.

In one example embodiment, the electronic device structure 104 is a thin-film transistor (TFT). An electronic transistor or a TFT may be characterized by different electrical characteristics such as threshold voltage (or turn on voltage) and source-drain current under different predetermined (gate and source-drain) voltage bias conditions.

When the substance selection structure 102 and the TFT 104 are electrically connected, the substance selection structure 102 may operate as a gate electrode of the TFT 104. In such configuration, the gate voltage signal may be applied to the TFT 104 via the molecular imprinted polymer 106. For example, a fix positive or negative gate bias may be applied using an electric source as the gate voltage bias, and the threshold voltage of the TFT 104 may be changed due to an interaction between the target substance 122 and the molecular imprinted polymer 106, therefore the source-drain current across the source and drain electrodes may be increased/decreased when compare to the drain current under a same external gate/source/drain voltage bias applied to the transistor without a target substance in contact with the molecular imprinted polymer layer 106.

Preferably, the electronic device structure 104 may comprises an active layer 112 such as a TFT material including silicon, a compound semiconductor, metal oxide semiconductor (e.g. zinc oxide) or an organic material such as copper hexadecafluorophthalocyanine (F16CuPc). A layer of dielectric material 114 may be included to serve as the gate dielectric of the TFT, and may include oxides such as $SiO_2$, $HfO_2$ and/or $Al_2O_3$. The source/drain electrodes 116 may include typical conductive metals with suitable work functions such as Au, Ag and or Al.

The electronic device structure 104 and the substance selection structure(s) 102 are electrically and/or physically connected, such that electrical signal may be transmitted between different individual structures. Preferably, the electrochemical detector 100 further comprises an intermediate substrate 118 arranged to connect one or more substance selection structure 102s and/or the electronic device. For example, the intermediate substrate 118 may include a copper substrate, or it may include an electrically conductive substrate, such as but not limited to an aluminum foil and a glass substrate coated with indium-doped tin oxide (ITO). The intermediate substrate 118 may also provide mechanical support to different structures disposed thereon.

Figure 3A:
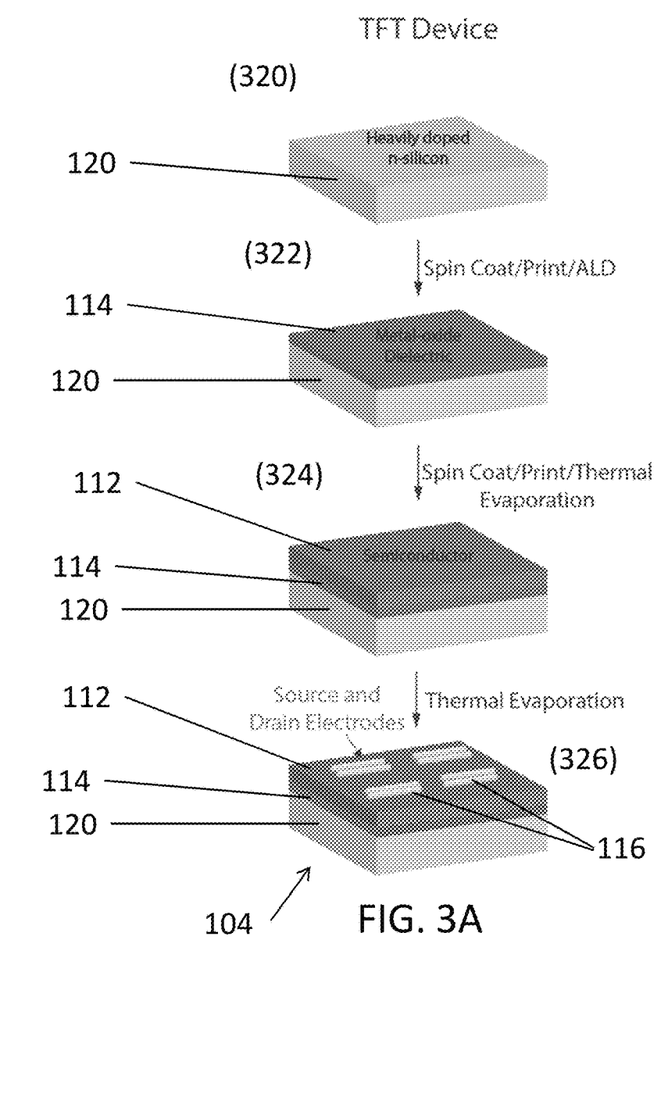
FIG. 3A is an illustration showing a process flow of fabrication of an electronic device structure of the electrochemical detector of FIG. 1.
Figure 3B:
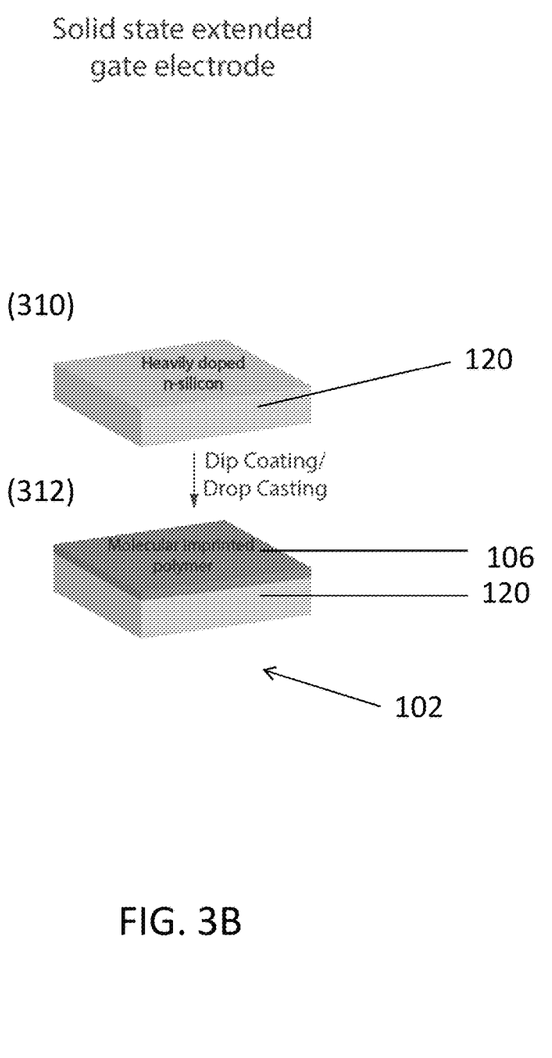
FIG. 3B is an illustration showing a process flow of fabrication of a substance selection structure of the electrochemical detector of FIG. 1.
Figure 3C:
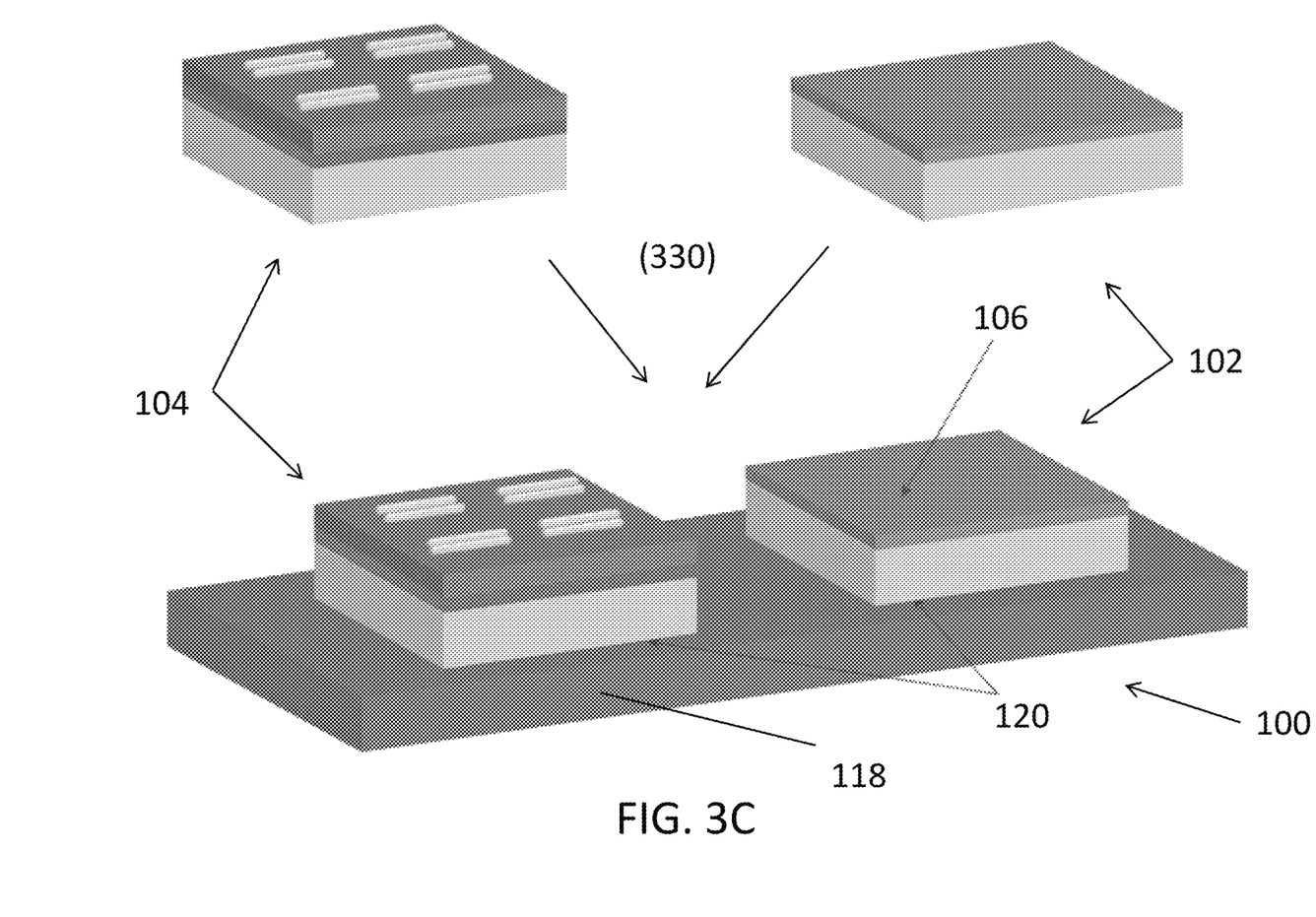
FIG. 3C is an illustration showing the combination of the electronic device structure of FIG. 2A and the substance selection structure of FIG. 2B in the fabrication of the electrochemical detector of FIG. 1.

With reference to FIGS. 3A to 3C, there is shown an example embodiment of a fabrication of the electrochemical detector 100. In this embodiment a substance selection structure 102 and an electronic device structure 104 are fabricated on a plurality of separate substrates 120 (such as heavily doped semiconductor substrates or metal substrates), and the two fabricated structures are physically and electrically connected to an intermediate copper substrate 118.

To fabricate the substance selection structure 102, at step 310, a heavily n-doped (n+) silicon substrate 120 is cleaned with standard cleaning procedures. At step 312, the molecular imprinted polymer 106 is deposited on the surface of the silicon substrate 120.

The molecular imprinted polymer (MIP) 106 may be prepared by mixing 14.5 mmol monomer (acrylamide or acrylic acid), 5.3 mmol cross-linker (N,N-methylene-biacrylamide), 0.7 mmol ammonium persulfate and 2.5 mmol template (Bis(2-ethylhexyl) phthalate, DEHP) in 25 mL Dimethylformamide and 10 mL DI water. After the solution was well mixed, the solution may be degassed by nitrogen, then 0.5 ml tetramethylethylenediamine (TEMED) may be added to initiate the fabrication. The solution may be kept for 16 hours in order to complete the polymerization. By completing such polemerization process, a combination of a molecular-imprinted polymer and a molecular template of the target substance (DEHP) is fabricated.

The fabricated combined MIP and template may be filtered, washed and dried under nitrogen atmosphere, and may then be ground and sieved to obtain a plurality of polymer particles each having a size of around 50 μm. The molecular template (DEHP) may then be extracted and removed from the MIP by the Soxhelt extraction in 24 hour with methanol. Finally, the MIP powder may be dried under a nitrogen atmosphere.

Preferably, the voids may be created after the DEHP template is extracted and removed from the MIP. In this example, acrylamide (monomer) belongs to the amide group, and phthalates belong to ester group. The formation of template-monomer complexes is due to the hydrogen bond prior to the polymerization reaction. This allows the template molecules to be embedded in the molecule post-polymerization.

Alternatively, the MIP may be fabricated for the detection of other target substances. In some other example embodiments, other phthalates, provided that they are able to form complexes prior to polymerization, may be used as templates in the fabrication of MIP layer 106.

Figure 6:
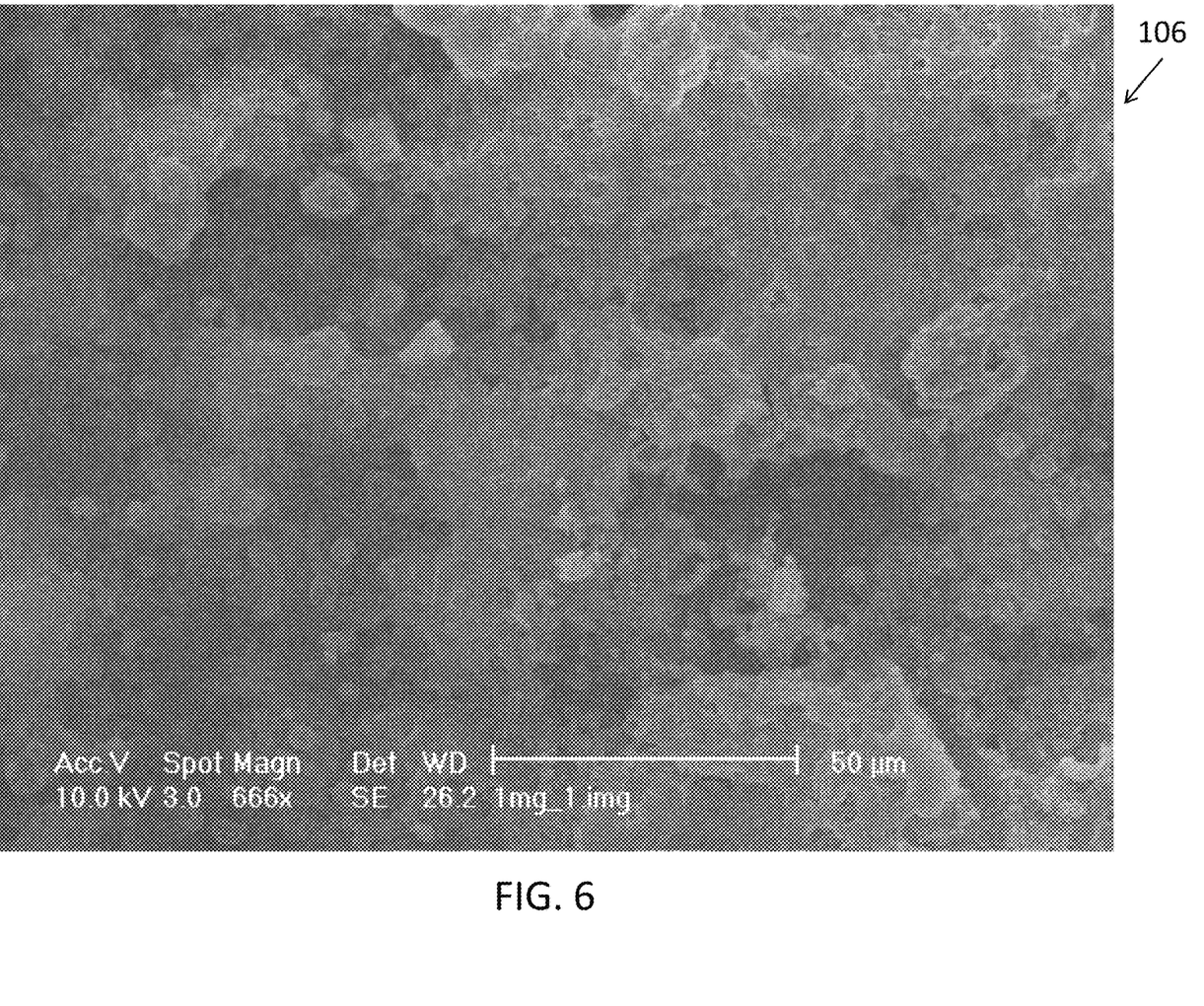
FIG. 6 is a scanning electron microscopy image of a molecular-imprinted polymer of the substance selection structure of the electrochemical detector of FIG. 1.

The MIP may be mixed with trichlorosilane (1 mg/mL) and dropped cast on the surface of the silicon substrate 120. Alternatively, any other solvent suitable for dissolving the MIP polymer particles may be used. The solvent may then be driven away in a following drying process (e.g. under a nitrogen atmosphere) so as to form the MIP layer 106. Referring to FIG. 6, there is shown an SEM image of the surface of the MIP layer 106.

Alternatively, the prepared MIP may be deposited on the clean silicon substrate 120 by any solution process such as spin coating, sol-gel, printing, spray coating and/or screen printing.

The thickness of the MIP layer 106 is preferably at approximately 50-100 μm. The performance of the electrochemical detector 100 may depend on the MIP particle size, in which the response time of the electrochemical detector 100 may be reduced by reducing the particle size. In addition, the response time may also be reduced by reducing the thickness of the MIP layer 106 on the substance selection structure 102, without affecting the detection limit and/or the linear dynamic range of the electrochemical detector 100.

To fabricate the TFT structure 104, at step 320, an n+ silicon substrate 120 is cleaned with standard cleaning procedures. At step 322, the metal-oxide dielectric (e.g. $HfO_2$, $Al_2O_3$) layer 114 is coated on top of the silicon substrate 120 using either solution process sol-gel method (spin coating, printing. etc.) or atomic layer deposition (ALD), and preferably the dielectric layer 114 has a thickness of 5 nm-10 nm. Preferably, such dielectric layer may operate as a gate dielectric of the TFT device.

At step 324, a semiconductor layer 112 (n-type semiconductor) is deposited using thermal evaporation or formed through a solution process sol-gel method (spin coating, printing. etc.) or any other suitable fabrication methods as discussed earlier. In this process, 30 nm-50 nm of semiconductor layer 112 is formed on top of the gate dielectric layer 114, which may operate as the active layer of the TFT device.

At step 326, gold or other suitable metal pads 116 are deposited on the semiconductor layer which form the source and drain electrodes of the TFT device 104. The metal pads 116 may be deposited with thermal evaporation through a shadow-mask with the desired patterns. Alternatively, a conformal layer of metal may be patterned using conventional photolithography approaches and other suitable deposition methods to form the metal pads 116. Preferably, the metal pads 116 may include a thickness of 30 nm-50 nm.

The abovementioned ranges of thickness of different layers may be changed in according to requirements or applications of the electrochemical detector 100.

The fabricated substance selection structure 102 and TFT structure 104 may be connected to the intermediate copper substrate 118 at step 330. For example, conductive adhesive may be applied to connect the two structures, either on the same side or opposite sides, to the copper substrate 118. In such configuration, the substance selection structure 102 may operate as an extended gate electrode of the TFT device 104. Alternatively, the substance selection structure 102 and the TFT structure 104 may be connected without an intermediate substrate 118, or the two different structures may be fabricated on the same substrate such as on a same side of a silicon substrate or on opposite sides on a double-side polished silicon substrate, in which the electrical signal between the two structures may be transmitted through the silicon substrate.

In yet another example embodiment, the MIP layer 106 may be fabricated with two or more molecule templates such that the detector 100 may detect the corresponding two or more target substances. Alternatively, multiple substance selection structures 102 each includes an MIP layer prepared with different molecular templates may be connected to the intermediate copper substrate 118, such that the electrochemical detector 100 may detect different target substances 122 applied to each of the different substance selection structures 102.

Figure 4:
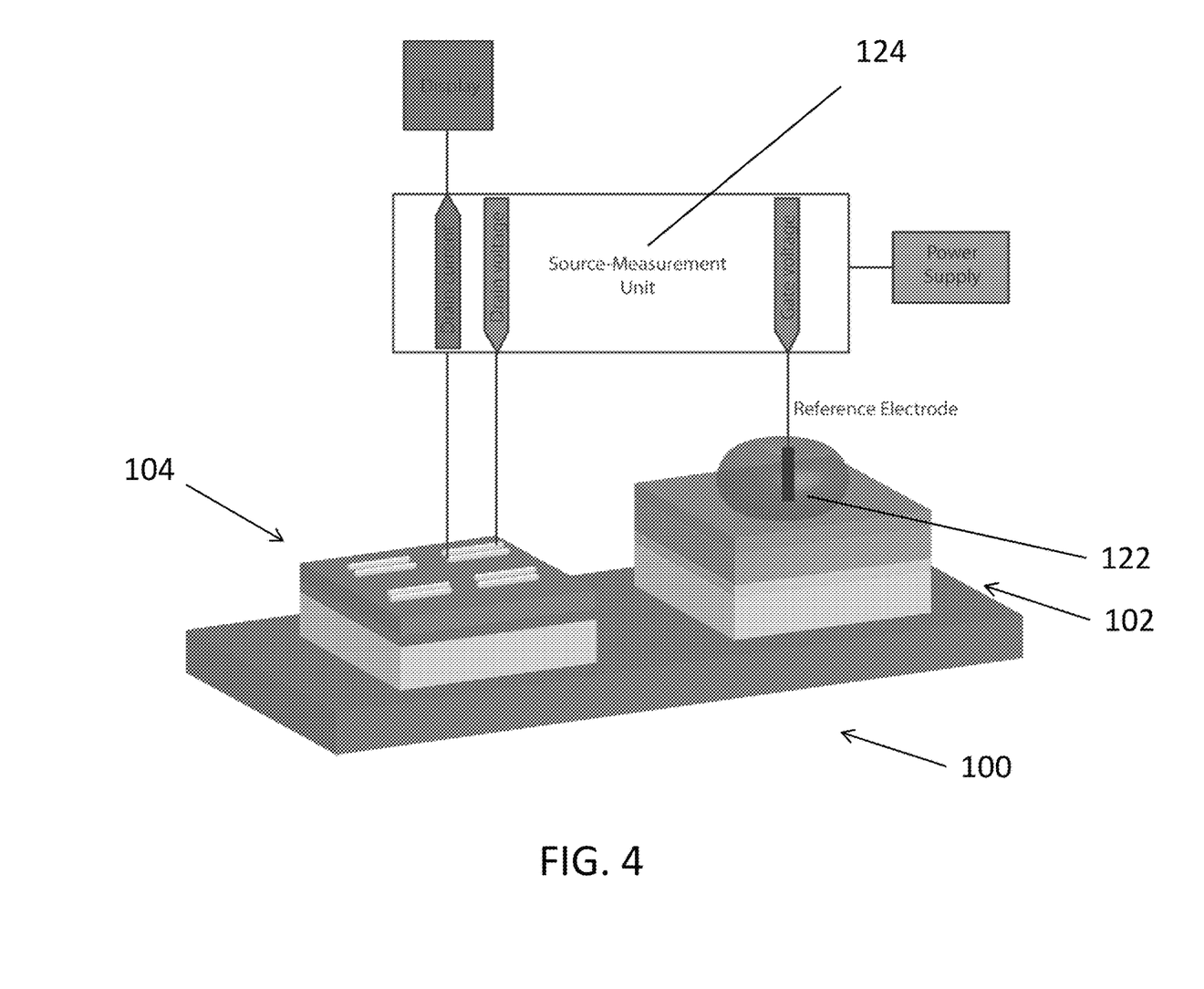
FIG. 4 is an illustration showing an example operation of detecting a target substance with the electrochemical detector of FIG. 1.

With reference to FIGS. 4A and 4B, there is shown an embodiment of a method of detecting a target substance with an electrochemical detector 100. The method comprises the steps of: applying an analyte solution 122 containing a predetermined amount of the target substance to the at least one substance selection structure 102; applying a gate voltage to the thin-film transistor 104 via the analyte solution 122 and the at least one substance selection structure 102; applying a source-drain bias to the thin-film transistor 104; and determining a concentration of the target substance in the analyte solution 122 based on a characterization of the electrical characteristic of the thin-film transistor 104.

In this example, an analyte solution 122 which contains the target substance such as DEHP is applied on a surface of MIP layer 106 of the substance selection structure 102. As discussed earlier in this disclosure, the when the MIP 106 accommodates one or more DEHP molecules 122 in the analyte solution which is in contact with the MIP layer 106, which leads to a change of permittivity/dielectric constant of the MIP layer 106, and may also lead to a change in a differential capacitance of the substance selection structure 102, the electrical characteristic of the electronic device structure 104 is altered. As a result, the threshold voltage and/or source-drain current are altered. Such change in electrical characteristics of the TFT device 104 corresponds to the concentration of the detected target substance in the analyte solution 122, and the change may be characterized by conventional electrical measurement unit for characterizing a transistor or other types of electronic devices.

For example, a high impedance (gigaohm) voltmeter, a nano-ammeter, a semiconductor parameter analyzer or an electrical source-meter unit (SMU) such as Keithley 2400 series may be used in the measurement steps. Example applied voltage bias may include a gate voltage of 3V and source-drain voltage of 3V. A small amount (such as 20-30 µL) of analyte solution is sufficient for the detection of the target substance.

In an example measurement setup, referring to FIG. 4, the analyte solution 122 is dropped on the extended gate sensor. A reference electrode is dipped into the sample solution 122. Using an SMU unit 124, a positive gate voltage is applied though the reference electrode and at the same time a positive drain-source voltage is applied to the TFT device 104. The signal is read out as a function of the threshold voltage shift of the TFT device 104 or the change in saturation drain current at a fixed gate voltage and source-drain voltage.

Figure 5A:
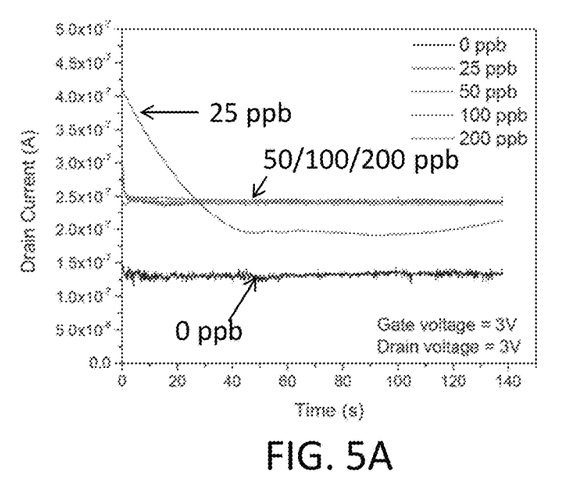
FIG. 5A is a plot showing a transient drain current curve for various concentrations of target substances based on the example operation of detecting a target substance of FIG. 4.
Figure 5B:
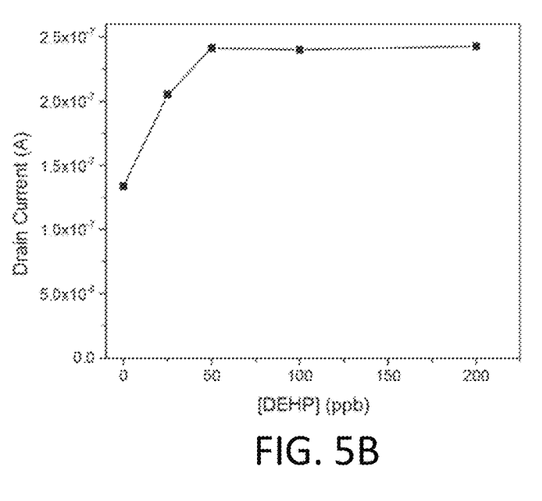
FIG. 5B is a plot showing calibrated values of the drain currents obtained in FIG. 5A.

With reference to FIGS. 5A and 5B, there is shown a measurement result for the detection of 0, 25, 50, 100 and 200 ppb DEHP in an analyte solution 122 with drain current range in the range of $2 \times 10^{-7}$ to $6 \times 10^{-7}$ A. it is shown that the electrochemical detector 100 has a detection range of 25 ppb to 50 ppb, a detection limit of around 25 ppb and a detection sensitivity of approximately $2 \times 10^{-9}$ A/ppb.

As the voids of the MIP fill up with increasing analyte concentration or the molecules of the target substance 122, there is an increase in drain current until the all the voids within the MIP are filled (saturation point). Upon reaching saturation, there are no further empty voids in the MIP to be filled. Therefore, there is no change in drain current with increase in analyte concentration beyond saturation.

Figure 5C:
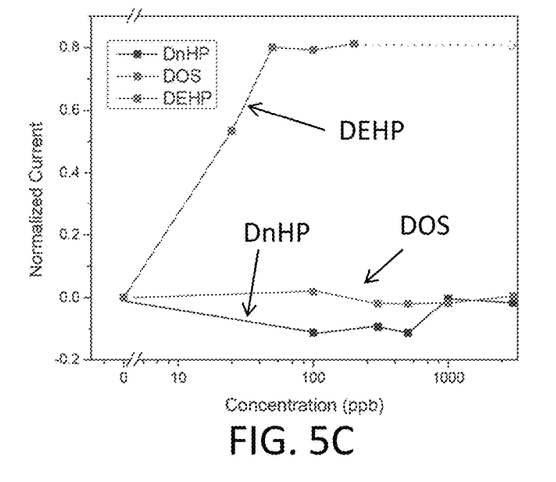
FIG. 5C is a plot showing a selectivity performance of the electrochemical detector of FIG. 1 in detecting a target substance and other substances.

With reference to FIG. 5C, there is shown a selectivity performance of the phthalate sensor 100 with DEHP imprinted polymer. The dotted line shows the predicted value of the normalized current for DEHP at 3000 ppb. It is shown that the electrochemical detector 100 has an excellent selectivity of DEHP (diethylhexyl phthalate) against DOS (dioctyl sebacate) and DnHP (Di-n-hexyl phthalate).

These embodiments are advantageous in that the electrochemical detector may be used in various applications including detection of harmful or toxic substances such as plasticizers. It may be implemented in portable electronic devices and hand-held sensors which may be used in domestic applications. The low-voltage operation of the electrochemical detectors ensures chemical stability (no induced electrolysis) of analyte solutions.

Advantageously, the performance of the detection shows that the electrochemical detector has high selectivity and sensitivity for target substance with the molecular-imprinted polymer electrode. The solid-state molecular-imprinted polymer layer may be easily tuned for selectively sensing different molecules (reversible & non-reversible), such as but not limited to DOS, DnHP, DBP, BBP, DNOP, DIDP, DINP by fabricating different MIP with different molecule templates. In addition, solid-state molecule-selective electrode (the extended gate) requires no internal filling solution.

The fabrication process is also simple and the electrochemical detector may be readily fabricated using different simple fabrication processes including low-cost fabrication methods such as printing and solution processing with low-cost materials. In addition, the substance selection structure and the electronic device structure may be separately fabricated on different substrates which may further simply the fabrication process involved. The fabrication of the electrochemical detectors may be easily scaled up.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. An electrochemical detector comprising:
   a substance selection structure disposed adjacent to a thin-film transistor (TFT) device structure, wherein the substance selection structure and the TFT device structure are separately fabricated on a first doped silicon substrate and a second doped silicon substrate, respectively, and
   a conductive intermediate substrate fixedly mounted to the first doped silicon substrate and the second doped silicon substrate such that the conductive intermediate substrate is directly in contact with the first and the second doped silicon substrates, thereby physically and electrically connecting the substance selection structure and the TFT device structure, wherein the conductive intermediate substrate includes a copper substrate;
   wherein:
      the TFT device structure includes a thin-film transistor having an active layer and source/drain electrodes, the thin-film transistor is formed on the second doped silicon substrate,
      the substance selection structure defines an extended gate electrode of the thin-film transistor, the substance selection structure includes a molecular imprinted polymer layer disposed on the first doped silicon substrate,
      the extended gate electrode and source/drain electrodes of the thin-film transistor are arranged in opposite sides of the active layer of the thin-film transistor, and the molecular imprinted polymer layer is arranged to interact with a target substance having a molecular structure so as to alter an electrical characteristic of the TFT device structure through the electrical connection formed by the first doped silicon substrate, the intermediate substrate and the second doped silicon substrate.

2. An electrochemical detector in accordance with claim 1, wherein the substance selection structure is arranged to interact with at least one molecule of the target substance.

3. An electrochemical detector in accordance with claim 2, wherein the substance selection structure includes a molecule-selective electrode.

4. An electrochemical detector in accordance with claim 3, wherein the polymer layer is arranged to accommodate the at least one molecule, and wherein the target substance is in contact with the molecular imprinted polymer layer.

5. An electrochemical detector in accordance with claim 4, wherein the molecular imprinted polymer layer includes a plurality of voids each arranged to accommodate a molecule of the target substance.

6. An electrochemical detector in accordance with claim 5, wherein the plurality of voids includes a structure matching with a molecular structure of the at least one molecule.

7. An electrochemical detector in accordance with claim 6, wherein the plurality of voids are selective to the target substance.

8. An electrochemical detector in accordance with claim 1, wherein the molecular imprinted polymer includes a plurality of polymer particles each having a size of 50 µm.

9. An electrochemical detector in accordance with claim 4, wherein the electrical characteristic of the TFT device structure is altered when the molecular imprinted polymer layer accommodates the at least one molecule.

10. An electrochemical detector in accordance with claim 9, wherein the electrical characteristic of the TFT device structure is altered by a change in a differential capacitance of the substance selection structure.

11. An electrochemical detector in accordance with claim 10, wherein the electrical characteristic of the TFT device structure is altered by a change in a permittivity and/or a dielectric constant of the molecular imprinted polymer layer accommodating the at least one molecule.

12. An electrochemical detector in accordance with claim 1, wherein the electrical characteristic includes a threshold voltage of the thin-film transistor.

13. An electrochemical detector in accordance with claim 1, wherein the electrical characteristic includes a saturation drain current across the thin-film transistor under a predetermined gate bias and a predetermined source-drain bias.

14. An electrochemical detector in accordance with claim 1, wherein the target substance includes plasticizer.

15. A method for fabricating an electrochemical detector in accordance with claim 1, comprising steps of:
   separately fabricating the substance selection structure and the TFT device structure respectively on the first and the second doped silicon substrates; and
   fixedly mounting the first and the second doped silicon substrates with the conductive intermediate substrate such that the conductive intermediate substrate is directly in contact with the first and the second doped silicon substrates, thereby physically and electrically connecting the substance selection structure and the TFT device structure.

16. A method for fabricating an electrochemical detector in accordance with claim 15, wherein the step of fabricating the substance selection structure comprises steps of:
   fabricating a combination of a molecular-imprinted polymer and a molecular template of the target substance using a polymerization process;
   extracting and removing the molecular template from the molecular-imprinted polymer; and
   depositing the molecular-imprinted polymer on the first doped silicon substrate to form a molecule-selective electrode.

17. A method for fabricating an electrochemical detector in accordance with claim 16, wherein the step of fabricating the substance selection structure further comprises a step of grounding and sieving the combination of the molecular-imprinted polymer and the molecular template to obtain a plurality of polymer particles each having a size of 50 µm.

18. A method for detecting a target substance with the electrochemical detector in accordance with claim 1, comprising steps of:
   applying an analyte solution containing a predetermined amount of the target substance to the substance selection structure;
   applying a gate voltage to the thin-film transistor via the analyte solution and the substance selection structure;
   applying a source-drain bias to the thin-film transistor; and determining a concentration of the target substance in the analyte solution based on a characterization of the electrical characteristic of the transistor.

\* \* \* \* \*